(12) United States Patent
Gregoire et al.

(10) Patent No.: US 11,395,731 B2
(45) Date of Patent: Jul. 26, 2022

(54) MICROANCHORS FOR KNOTLESS TISSUE REPAIR

(71) Applicant: Smith & Nephew, Inc., Memphis, TN (US)

(72) Inventors: David K. Gregoire, Mission Viejo, CA (US); George W. White, Corona, CA (US)

(73) Assignee: Smith & Nephew, Inc., Memphis, TN (US)

( * ) Notice: Subject to any disclaimer, the term of this patent is extended or adjusted under 35 U.S.C. 154(b) by 340 days.

(21) Appl. No.: 16/717,674

(22) Filed: Dec. 17, 2019

(65) Prior Publication Data

US 2020/0121445 A1 Apr. 23, 2020

Related U.S. Application Data

(62) Division of application No. 15/557,694, filed as application No. PCT/US2016/020846 on Mar. 4, 2016, now Pat. No. 10,543,075.

(Continued)

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61B 17/0469* (2013.01); *A61B 17/0485* (2013.01); *A61B 17/06166* (2013.01); *A61B 2017/00345* (2013.01); *A61B 2017/00526* (2013.01); *A61B 2017/044* (2013.01); *A61B 2017/0412* (2013.01); *A61B 2017/0414* (2013.01); *A61B 2017/0445* (2013.01);

(Continued)

(58) Field of Classification Search
CPC ........ A61F 2240/001; A61F 2220/0058; A61F 2220/0016; A61F 2002/0888; A61F 2002/0841; A61F 2/0811; A61B 2017/06185; A61B 2017/0458; A61B 2017/0445; A61B 2017/044; A61B 2017/0414; A61B 2017/0412; A61B 2017/00526; A61B 17/0485; A61B 17/0469; A61B 17/0401
See application file for complete search history.

(56) References Cited

U.S. PATENT DOCUMENTS

2005/0107828 A1* 5/2005 Reese ................ A61B 17/0401
606/232
2013/0096611 A1* 4/2013 Sullivan ............. A61B 17/0485
606/232

* cited by examiner

*Primary Examiner* — Jocelin C Tanner
(74) *Attorney, Agent, or Firm* — Norman F. Hainer, Jr.

(57) ABSTRACT

A knotless anchor for attachment of tissue to bone includes a rigid anchor body and a suture extending there from. The suture is hollow and includes a fixed limb portion secured to the rigid anchor body. A soft suture tunnel extends in a longitudinal direction through the fixed limb portion of the suture. A free suture limb is passed through the tissue, back to the anchor, and through the soft suture tunnel, thereby creating a closable suture loop around the tissue. Tension applied to the free suture limb closes the suture loop, and approximates the tissue to the anchor body. When the anchor is deployed in a bone hole, external features of the anchor body grip the walls of the bone hole and simultaneously compress the suture, thereby preventing tissue pull-out. Anchor assemblies and methods of tissue fixation are also disclosed.

20 Claims, 6 Drawing Sheets

Related U.S. Application Data

(60) Provisional application No. 62/132,994, filed on Mar. 13, 2015.

(51) Int. Cl.
*A61B 17/06* (2006.01)
*A61B 17/00* (2006.01)

(52) U.S. Cl.
CPC ................ *A61B 2017/0458* (2013.01); *A61B 2017/06185* (2013.01); *A61F 2002/0841* (2013.01); *A61F 2002/0888* (2013.01); *A61F 2220/0016* (2013.01); *A61F 2220/0058* (2013.01); *A61F 2240/001* (2013.01)

MICROANCHORS FOR KNOTLESS TISSUE REPAIR

CROSS-REFERENCE TO RELATED APPLICATIONS

This application is a divisional of U.S. application Ser. No. 15/557,694 filed Sep. 12, 2017, which is a 371 application of International Application No. PCT/US2016/020846, filed Mar. 4, 2016, entitled "MICROANCHORS FOR KNOTLESS TISSUE REPAIR," which claims priority to and benefit of U.S. Provisional Application No. 62/132,994, filed Mar. 13, 2015, the contents of which are incorporated herein by reference in their entirety for all purposes.

FIELD

The present disclosure is generally directed to anchors for approximating a tissue to bone and, more particularly to microanchors for knotless tissue repair.

BACKGROUND

There is an increasing demand for more types of minimally invasive surgical techniques. Because endoscopic and arthroscopic surgery tends to result in lower morbidity than open surgery, the minimally invasive surgical techniques are very appealing to both patients and physicians. These technologically-advanced procedures include many forms of soft tissue to soft tissue repairs and soft tissue to bone repair. Examples of these procedures in orthopedic surgery include rotator cuff repair, labral repair, biceps tenodesis, and anterior cruciate ligament reconstruction. Other examples in other surgical subspecialties include, but are not limited to, hernia repair, hysterectomies, and laparoscopic gastric bypass.

Many of the above mentioned tissue repair procedures involve approximating the tissue to a bone by deploying an anchor into the bone, and tying the tissue to the anchor with a suture. In a number of suture anchors, the suture is passed through an eyelet located on the proximal end of the anchor and passed through the tissue. (See, for example, U.S. Patent Publication No. 2002/0052629 and U.S. Pat. No. 5,370,662, where a suture is passed through an eyelet located on the proximal end of the anchor.) In order to use these suture anchors, however, the diameter of the hole drilled into the bone is generally in excess of 2.5 mm due to the need to manage four or more suture limbs, the anchor body, and the eyelet structure. While this may be acceptable in certain procedures, there are a number of procedures that would benefit from a smaller bone hole. For example, the procedure for reattaching the labrum to the acetabular rim in a hip repair would benefit by use of a smaller bone hole. It is therefore desirable to reduce the diameter of both the anchoring structure and the bone hole. Reducing the size of the bone hole and the anchor tends to make the tissue repair less traumatic and leads to a shorter patient recovery time.

SUMMARY OF THE DISCLOSURE

Described herein is a knotless anchor for securing a tissue to a bone in a human or animal including a rigid anchor body and a suture secured thereto. As described further herein, the parallel direction or orientation of a suture tunnel reduces the number of suture limbs required to fixate a tissue to bone. The reduction in the number of suture limbs arises because the suture itself forms the eyelet, eliminating the need of a separate laterally-disposed eyelet structure. It is estimated that the effective diameter is reduced by an amount equal to at least the cross sectional area of one suture plus the cross sectional area of the eyelet mechanism. Additionally, the bone fixation features compress the suture between the bone wall and an exterior surface of the rigid anchor body when the anchor body is deployed in a bone hole. Embodiments described herein bind the suture and prevent tissue pull out. Advantageously, the anchor operates without the need to tie a knot, without adding blocking protrusions or obstacles along the suture, and without use of multiple actuatable/moving internal components for clamping the suture.

In embodiments, the suture and the rigid anchor body are securely connected by bonding, heat staking, ultrasonic welding or staking, ultrasonic molding, or injection molding.

In embodiments, the fixed limb portion of the suture includes a suture tunnel. The suture tunnel commences at a suture entry port and terminates at a suture exit port.

In embodiments, the rigid anchor body comprises at least one bone locking feature such as but not limited to an exterior barb, ridge, thread, or rib.

In embodiments, the suture is locked by compressing the suture between an exterior surface of the anchor body and the interior surface of the bone hole.

In embodiments, an anchor assembly comprises an anchor as described above and a snare extending through the suture eyelet. The snare is configured to draw the free end of the suture through the eyelet. The anchor assembly may also include an inserter tube for supporting and manipulating the anchor into the bone hole.

In embodiments, the anchor assembly may also include an advancer (or die) tube abutting the proximal end of the anchor body and for holding the anchor body in the bone hole as the inserter tube is retracted.

In embodiments, a method of anchoring a tissue to a bone of a human or an animal without tying a knot comprises passing a free suture limb through the tissue. The fixed suture limb is secured to a rigid anchor body. The free suture limb is drawn through a suture tunnel formed in the fixed suture limb thereby defining a closable suture loop around the tissue. The tissue is approximated towards the anchor body by closing the suture loop. The anchor body is inserted into a bone hole whereby the suture is compressed between an internal wall of the bone hole and an exterior feature of the anchor body thereby locking the suture and affixing the tissue to the bone.

In embodiments, the method further comprises providing the fixed suture limb on an exterior of the anchor body.

In embodiments, a multi-row tissue fixation method for anchoring a tissue to a bone without tying a knot comprises providing a first and a second rigid anchor body. A fixed suture limb is joined to each of the rigid anchor bodies. A free suture limb extends from each of the anchor bodies. The method further comprises deploying the first and second anchor bodies in first and second bone holes respectively. The free suture limbs are passed through the tissue. The tissue is approximated to the bone by applying tension to the free suture limbs of the first and second sutures until the tissue is positioned as desired.

In embodiments, the multi-row tissue fixation method further comprises threading the first and second free suture limbs through at least a third anchor body.

In embodiments, the multi-row tissue fixation method further comprises threading the first and second free suture limbs through third and fourth anchor bodies respectively.

In embodiments, the multi-row tissue fixation method further comprises deploying the third and fourth anchor bodies in third and fourth bone holes respectively.

In embodiments, the multi-row tissue fixation method further comprises creating the third and fourth bone holes in lateral locations relative to the first and second bone holes, the first and second bone holes being medially disposed.

In embodiments, a multi-row tissue fixation method further comprises a first suture having a non-hollow or tape-like shape.

Aspects of the present disclosure advantageously improve upon some of the previous anchor designs by, amongst other things, reducing the footprint of the bone hole.

BRIEF DESCRIPTION OF THE DRAWINGS

The foregoing and other features will be apparent from the following description of particular embodiments disclosed herein, as illustrated in the accompanying drawings.

FIGS. 1b-c are details of the interface between the soft suture tunnel and the anchor body of FIG. 1a;

DETAILED DESCRIPTION

Before the present disclosure is described in detail, it is to be understood that this disclosure is not limited to particular variations set forth herein as various changes or modifications may be made to the disclosure described and equivalents may be substituted without departing from the spirit and scope of the disclosure. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. In addition, many modifications may be made to adapt a particular situation, material, composition of matter, process, process act(s) or step(s) to the objective(s), spirit or scope of the present disclosure. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the disclosure. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application. Nothing herein is to be construed as an admission that the present disclosure is not entitled to antedate such material by virtue of prior disclosure.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this disclosure belongs.

Figure 1A:
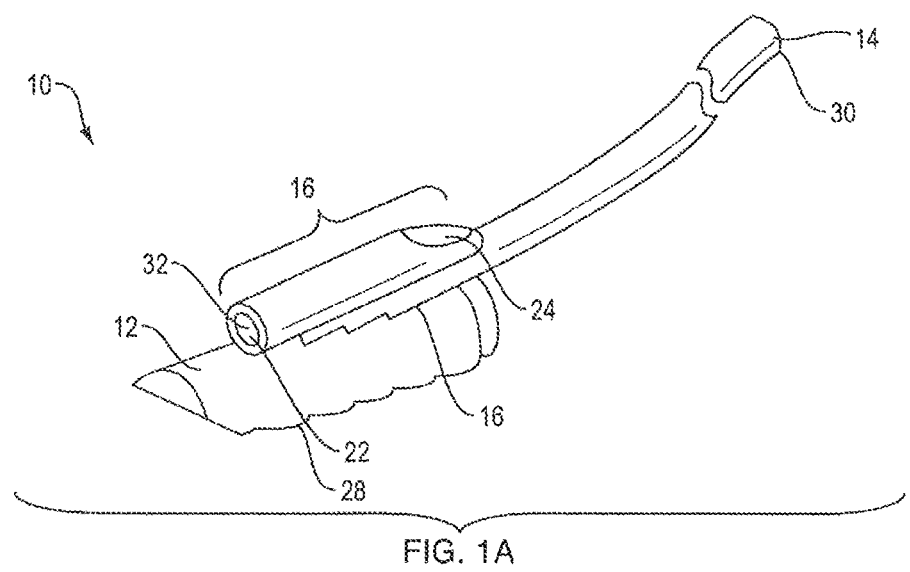
FIG. 1a is a perspective view of an anchor comprising a soft suture tunnel secured to an exterior surface of the anchor body.

With reference to FIG. 1a, for example, a knotless anchor 10 for securing soft tissue to bone is shown. In embodiments, the anchor 10 comprises a rigid anchor body 12, and a length of suture 14 secured to an external surface of the anchor body 12. The anchor body 12 may comprise a single or unitary rigid body. A fixed end 16 of the suture 14 is secured along the exterior of the anchor body 12. The fixed end 16 is shown affixed between the proximal and distal end of the anchor body 12. As described further herein, the other end of the suture 14 is a free end 30 and is threaded through the tissue to be approximated to the bone. Exemplary materials for the suture 14 are PGA, PGLA, or Ultra-high-molecular-weight polyethylene (namely, UHMWPE). The suture 14 is preferably hollow and braided. The suture 14 may have a variable pitch of the yarn. In embodiments, the suture 14 has a low pitch, permitting the hollow braid to more easily expand over the anchor body 12 than a high pitch braid. In embodiments, a section of flat tape (not shown) is incorporated into the suture 14 in order to spread tension load where the tape/suture is to contact the tissue.

In the embodiment shown in FIG. 1a, the suture 14 is a soft hollow member (e.g., a hollow braid). It is secured in a predominantly parallel orientation to the longitudinal axis of the anchor body 12. The fixed end 16 of the suture 14 operates as an eyelet for passage of the free end 30. A first port 22 and a second port 24 are shown in the hollow braided suture 14. The first port 22 and the second port 24 can be used be as a suture entry port and suture exit port respectively. Alternatively, the first port 22 could be used as an exit port and the second port 24 could be used as an entry port. A suture lumen or tunnel 32 extends parallel to the axis of the anchor body 12 and connects the first port 22 to the second port 24. The free end 30 of the suture 14 is passed through tissue, then through tunnel 32, resulting in only three limbs extending from the bone hole (rather than four limbs), advantageously providing a reduced diameter when compared to other anchor designs.

With reference again to FIG. 1a, the length of the tunnel 32 may range from about 1 mm to about 12 mm. The diameter of the tunnel 32 may range from about 0.2 mm to about 2 mm. The tunnel 32 and suture 14 are preferably unitary continuous components of the knotless anchor 10, and not separate members or assemblies which can undesirably make the anchor footprint larger and more complex. The cross section of the knotless anchor 10 (i.e., suture 14 plus anchor body 12) is about the same diameter as the suture 14 itself, or maybe slightly larger (e.g., 10-15%, or up to 25% larger) to accommodate the diameter of the anchor body 12. Bone fixation features, such as ridges 28, are shown on the anchor body 12. However, the bone fixation features may vary widely. Screw threads, barbs, ribs, protrusions, or a smooth shell can be utilized to secure the anchor body 12 in bone. The bone fixation features serve to grip internal walls of the bone hole when the anchor body 12 is installed.

Figure 1B:
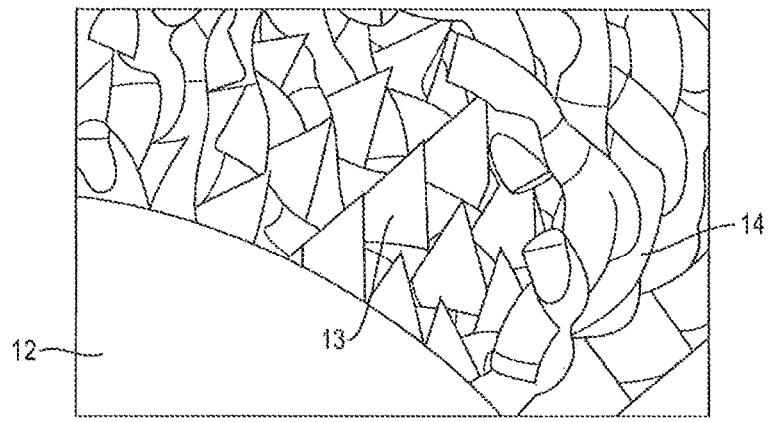
Figure 1C:
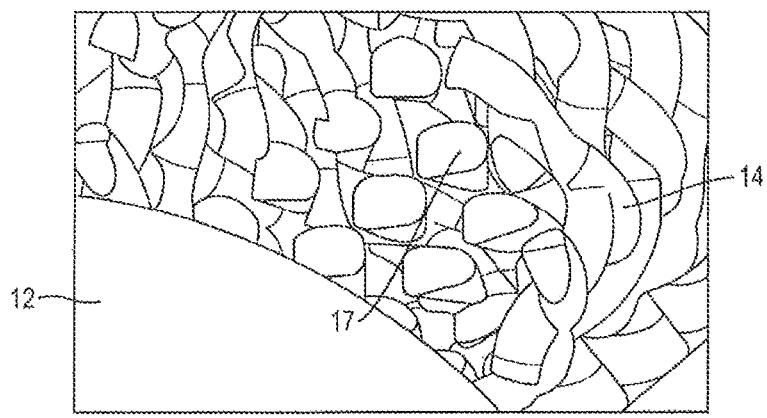

As detailed in FIG. 1b, the suture 14 and the anchor body 12 may be connected in various ways. For example, the suture 14 can be connected to the anchor body 12 via bonding, ultrasonic welding or staking, or heat staking. Mechanical interlocking features 13 incorporated into the anchor body 12 that pierce or engage the suture 14 may aid the assembly process. The materials and size of the anchor body 12 and suture 14 may be selected such that the melt temperature of the anchor body 12 is lower or equal to the melt temperature of the suture 14 for ease of assembly. Alternatively, if the melt temperature of the anchor body 12 is higher than the melt temperature of the suture 14, the attachment can still be formed because the actual polymer melt profile can be a lower temperature at the suture interface and managed to limit damage to the suture 14. As shown in FIG. 1c, displacement and or deformation 17 of mechanical interlocking features 13 (FIG. 1b) on the anchor body 12 that engage the suture 14 via ultrasonic welding or staking, or heat staking is a suitable assembly process to limit damage to the suture 14. Suitable materials for the anchor body 12 include without limitation PEEK, PLLA, REGENESORB™ (manufactured by Smith & Nephew plc, London England), and other biocompatible or bioabsorbable materials. Insert molding the anchor body 12 to the suture 14 via ultrasonic molding or injection molding are also viable assembly methods. In embodiments, the suture 14 is connected to the anchor body 12 without a knot.

Figure 2:
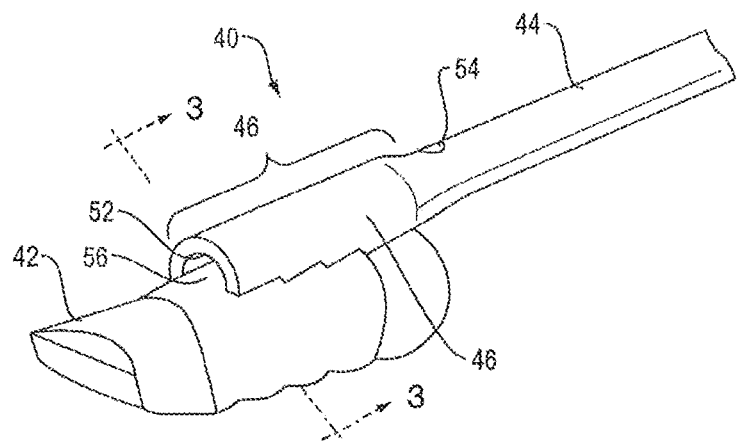
FIG. 2 is a perspective view of another anchor comprising a soft suture tunnel partially incorporated into the anchor body.
Figure 3:
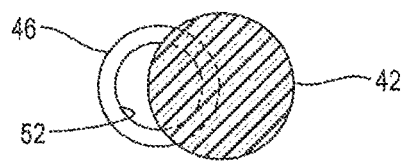
FIG. 3 is a cross sectional view of the anchor shown in FIG. 2, taken along line 3-3.

FIG. 2 illustrates an alternative embodiment of a knotless anchor 40 for attaching tissue to bone. Anchor 40 is similar to the anchor 10 shown in FIG. 1a except that the suture 44 is partially integrated into (insert molded, bonded, or staked to) the anchor body 42. The fixed end 46 of the suture 44 can be joined to the anchor body 42 via heat staking or molding. A suture tunnel 56 extends from the first port 52 to the second port 54. The suture tunnel 56 acts as an eyelet running parallel to the longitudinal axis of the anchor body 42. As described herein, incorporating the suture tunnel 56 along the longitudinal axis of the anchor body 42 reduces the diameter of the anchor 40 compared to anchors having a tunnel (or eyelet) perpendicular to the anchor body. FIG. 3 shows a cross-sectional view of the anchor 40 shown in FIG. 2, taken along line 3-3

Figure 4:
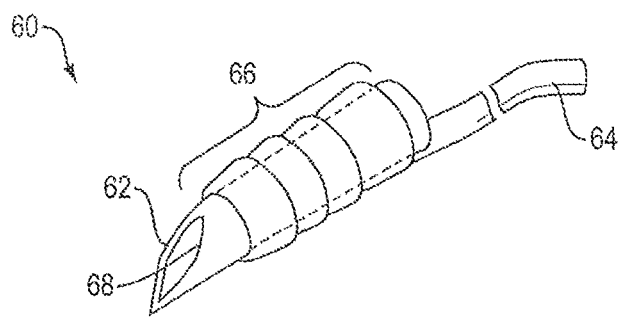
FIG. 4 is a perspective view of another anchor including a hard suture tunnel extending through the anchor body.

FIG. 4 shows another knotless anchor 60 for attaching tissue to bone. The anchor 60 shown in FIG. 4 is similar to the anchor 10 shown in FIG. 1a except that both the anchor body 62 and the suture 64 have a suture tunnel 68 extending in the longitudinal direction. The fixed end 66 circumferentially or radially surrounds the hard anchor body 62. The anchor 60 shown in FIG. 4 thus comprises a hard tunnel coaxially arranged within a soft tunnel.

Figure 5A:
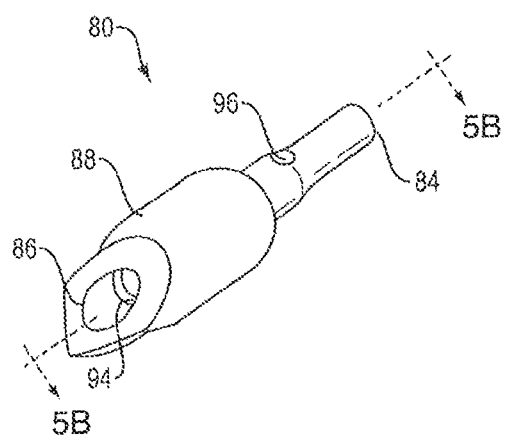
FIG. 5a is a perspective view of another anchor including a suture tunnel extending through the anchor body.

FIG. 5a shows another knotless anchor 80 for attaching tissue to bone. The anchor 80 shown in FIG. 5a is similar to that shown in FIG. 4 except the fixed end 84 is secure internally to the anchor body 88. More specifically, the fixed end 84 is secure within hard lumen 86 of the anchor body 88. The fixed end 84 includes a first port 94 and a second port 96. Therefore, in anchor 80, the axially or longitudinally disposed soft tunnel is coaxially arranged within the hard tunnel.

Figure 5B:
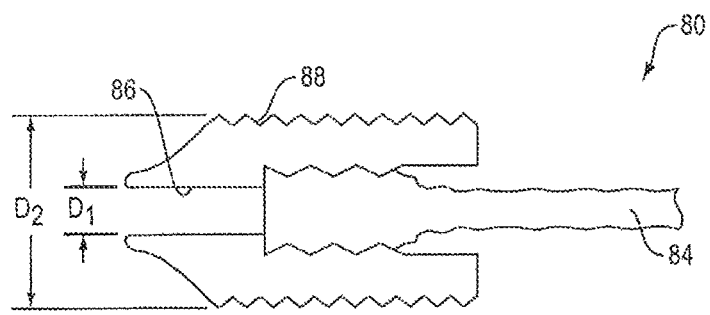
FIG. 5b is a cross sectional view of the anchor shown in FIG. 5a, taken along line 5b-5b.

With reference to FIG. 5b, a cross-sectional view of the anchor 80 is shown, taken along line 5b-5b. A preferred range for the internal diameter $D_1$ of the lumen 86 is about 0.5 mm to about 8 mm. A preferred range for the outer diameter $D_2$ of anchor body 88 is about 1.2 mm to about 2.5 mm. However, it is to be understood that the anchor 80 may have other dimensions.

FIGS. 6-10 illustrate a method of deploying an anchor 116 and approximating tissue 104 to bone 110. Although the anchor 116 shown in FIGS. 6-10 is similar to anchors described above in connection with FIGS. 5a-5b, other anchor configurations may be utilized in accordance with methods described herein.

Figure 6:
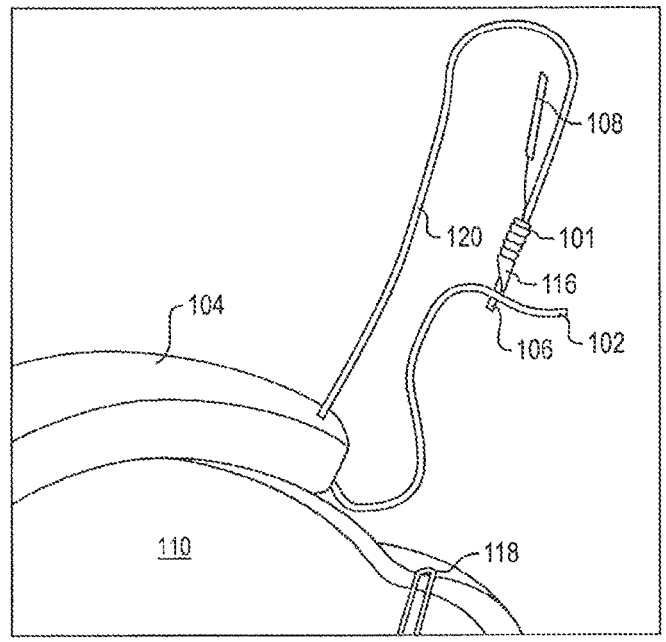
FIGS. 6-10 are illustrations of a method for approximating a tissue to bone.

FIG. 6 shows an anchor 116 comprising a fixed suture end 101 secured to the anchor 116 and a free suture end 102 which has been passed through tissue 104. A non-limiting example of a suture passer to deliver the suture free end through the tissue is the ACCU-PASS device manufactured by Smith & Nephew Corporation, Austin Tex., U.S.A. FIG. 6 also shows the free suture end 102 fed into a snare loop 106 having snare handle 108.

Figure 7:
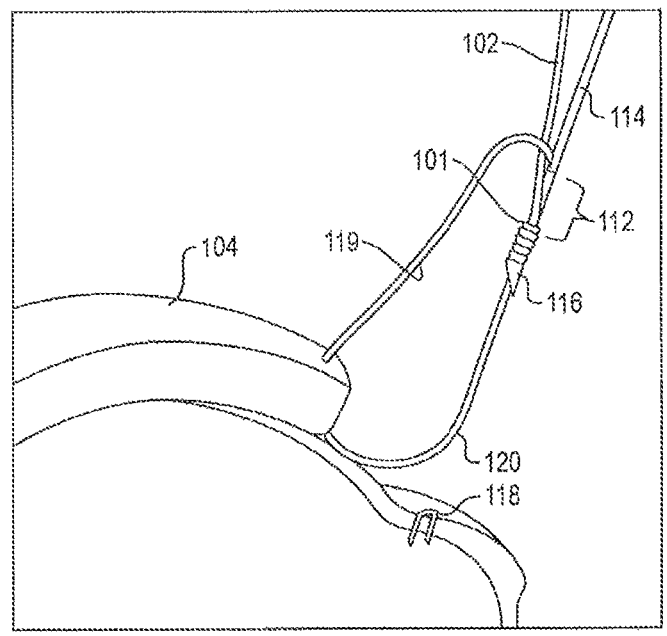
Figure 8:
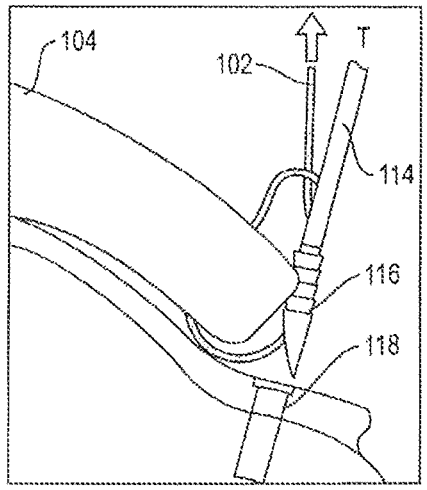

Next, and with reference to FIG. 7, snare handle 108 (FIG. 6) is pulled, drawing the free suture end 102 through the anchor 116. Free suture end 102 is drawn through the longitudinally disposed soft eyelet 112 formed by the suture 120. Stated alternatively, the suture 120 is drawn through (or fed into) itself. As free suture end 102 is further pulled, a closable loop 119 is formed and drawn over a portion of the tissue 104. Thus, a suture path commences at the fixed suture end 101 on the anchor 116, extends through the tissue 104, and returns to the anchor 116, continues through the soft eyelet 112 of the suture 120, and terminates at the free suture end 102. Free suture end 102 may be pulled by the physician to the desired tensional force. With reference to FIG. 8, tension (T) is applied to the free suture end 102 until a desired level of force or resistance is achieved. Tissue 104 is now shown in close proximity or adjacent anchor body 116.

Figure 9:
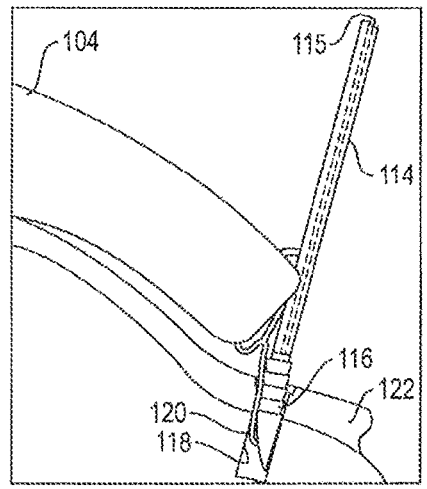

With reference to FIG. 9, an inserter 114 is shown mating with a proximal surface of the anchor body 116. The inserter 114, as described herein, assists with positioning the anchor 116 in the bone hole 118. Additionally, in embodiments, the inserter 114 may comprise an internal, axially slidable die member 115 to cooperate with an internal key hole (not shown) of the anchor 116. The inserter 114 holds the anchor 116 in place as the internal die member 115 is retracted. The components of the inserter 114 cooperate together to place, hold, and deploy the anchor 116 in the bone hole. Non-limiting examples of inserter members, dies, and handles are described in, for example, U.S. Pat. No. 6,780,198 to Gregoire et al.

FIG. 9 also illustrates the anchor 116 being inserted into a pre-drilled bone hole 118. However, in embodiments, anchor 116 may be pounded directly into a bone, creating the bone hole 118 as it is pounded into the bone. In embodiments, the distal end of the anchor 116 includes a hard, pointed edge to facilitate cutting through the bone. The anchor 116 may also include self-tapping threads to dig and grip the bone. In the assembly shown in FIG. 9, the suture 120 is compressed between the interior wall of the bone hole 118 and the rigid exterior surface of the anchor 116. Ridges on the surface of the anchor (FIG. 1) make contact with the suture 120 and securely hold the suture 120 in place. The suture 120 is compressed and locked. The anchor 116 may be adjusted to a depth, as shown, safely below the relatively hard cortical bone layer indicated by reference numeral 122.

Figure 10:
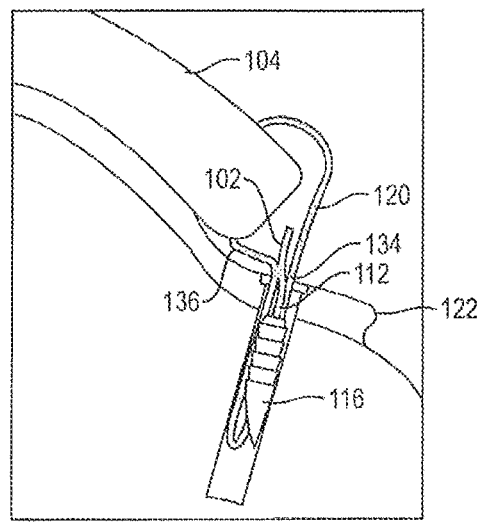

FIG. 10 shows the tissue 104 secured to the bone. The inserter 114 removed, and the free suture end 102 trimmed. Notably, the embodiment shown in FIG. 10 includes only three suture limbs 102, 134, 136 extending from the anchor 116. This reduction in the number of suture limbs arises from the soft eyelet 112 present along the longitudinal axis. Consequently, a larger laterally-disposed eyelet (or other type of suture loop/connector) is not necessary for tissue fixation.

Figure 11:
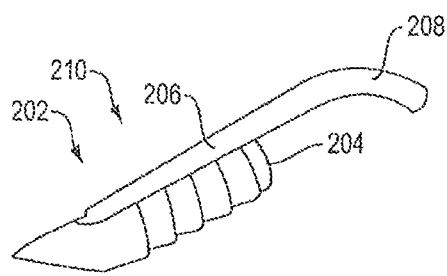
FIG. 11 is a perspective view of another anchor for approximating a tissue to bone.

FIG. 11 shows another anchor 202 including a rigid anchor body 204 and a suture 206 secure thereto. The embodiment shown in FIG. 11, however, differs from the previous described embodiments in that the anchor 202 does not feature a suture tunnel or eyelet. The fixed suture end 210 is preferably a suture tape or non-hollow suture. The free suture end 208 is directly affixed to a lateral aspect of the rigid anchor body 204. Alternatively, the free suture end 208 may be bonded, staked, or joined internally to anchor body 204. The tape or non-hollow suture is preferred in this embodiment so as to reduce the diameter or footprint of the bone hole. As described herein, anchor 202 can be useful in double or multi-row tissue fixation procedures. In another embodiment, the rigid anchor body 204 may include a hole (not shown) traversing the longitudinal axis to serve as an eyelet or insertion aid.

Figure 12:
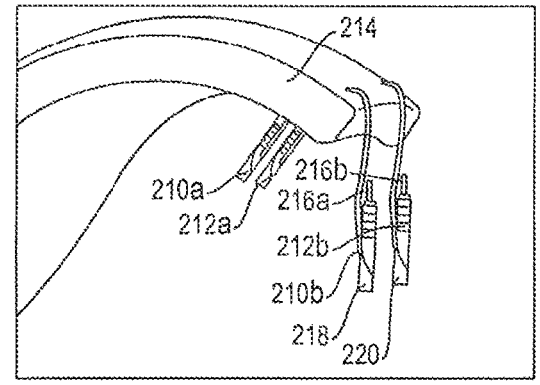
FIGS. 12-13 are illustrations of multi-row tissue fixation methods for approximating tissue to a bone.

FIG. 12 is an illustration of a multi-row tissue fixation technique comprising a first set of anchors 210a, 210b and a second set of anchors 212a, 212b. The second or additional set 212a, 212b are intended to provide better purchase on the tissue 214. In a double row procedure, medial anchors 210a, 212a (an example of which is shown in FIG. 11) may be pounded or installed into the medial bone holes. Free suture ends 216a, 216b are passed through the tissue 214 (e.g., a labrum or tendon). Free suture ends 216a, 216b are snared or otherwise threaded through suture eyelets of the lateral anchors 210b, 212b. Lateral anchors 210b, 212b may include the self-contained suture tunnels as described above. Tension is applied to free suture ends 216a, 216b until a desired force across the tissue 214 is achieved. The lateral anchors 210b, 212b are then deployed in the bone holes 218, 220, thereby locking the suture and anchors in the bone holes. The free suture ends 216a, 216b are trimmed.

The above-described double row technique utilizes smaller-diameter implants, and consequently reduces the size of the bone hole. In particular, in embodiments, less than four suture limbs (or in some embodiments less than three suture limbs) are necessary to carry out the tissue fixation procedure. The medial anchors 210a, 212a, for example, have only one suture limb extending therefrom, the suture being non-hollow or flat. Additionally, the lateral anchors 210b, 212b show only two suture limbs extending from the proximal end of the anchor. Smaller diameter bone holes and hardware are therefore enabled by the anchors and procedure described in connection with FIGS. 11-12.

Figure 13:
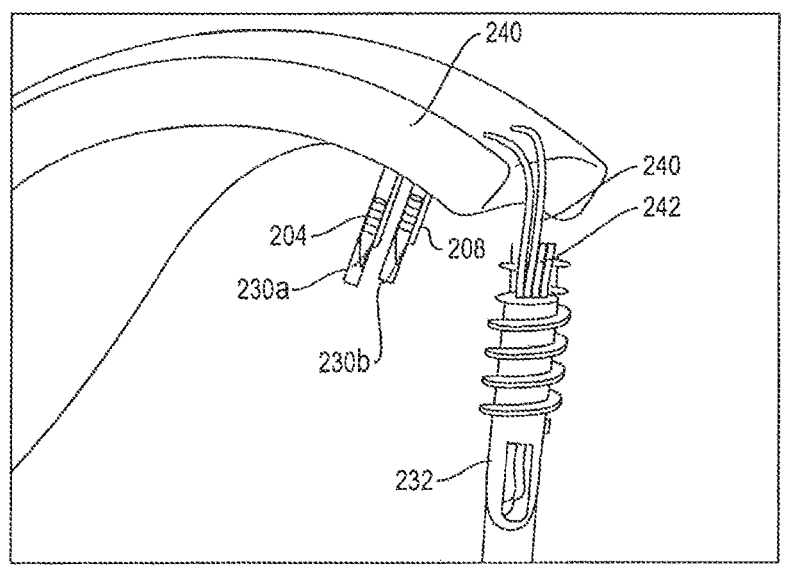

FIG. 13 is an illustration of another multi-row tissue fixation technique comprising a first set of medial anchors 230a, 230b and a second anchor 232. The technique shown in FIG. 13 is similar to that shown in FIG. 12 except that the two suture free ends 240, 242 are shown threaded through sole lateral anchor 232. Lateral anchor 232 has an internal lumen to accommodate both suture free ends 240, 242, and features a suture lock wholly independent of the bone lock mechanisms. For example, the anchor may be deployed in the bone hole, and after the anchor is properly seated in the bone hole, the suture may be tensioned and then locked within the anchor. A non-limiting example of an anchor similar to the anchor 232 shown in FIG. 13 is the Speed-Screw Knotless Fixation Device (Manufactured by Arthrocare Corporation, Austin, Tex.). The sutures are then trimmed.

Although FIGS. 11-13 illustrate double row configurations, the disclosure is not so limited. In embodiments, at least three rows of anchors may be deployed to achieve better tissue purchase and stability. Additionally, a number of non-limiting examples of multi- or double row techniques may be combined with aspects described herein including, without limitation, the multi-row fixation techniques described in connection with the Speedscrew™, Labralock™, and Speedlock™-brand knotless implants manufactured by ArthroCare Corporation, Austin Tex., U.S.A., and the suture described in U.S. Pat. No. 8,818,326 to Gagliano.

Although the present disclosure is suitable for attaching the labrum to the acetabular rim in a hip surgery, it is also applicable to other tissue fixation procedures including attachment of the rotator cuff tendon to the humeral head, or other tissue to bone and tissue to tissue procedures. Indeed, the present disclosure is suitable for hip, shoulder, and small joint repair. It is particularly desirable for repairs requiring a relatively small footprint.

While preferred embodiments of this disclosure have been shown and described, modifications thereof can be made by one skilled in the art without departing from the scope or teaching herein. The embodiments described herein are exemplary only and are not intended to be limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A method of anchoring a tissue to a bone of a human or an animal without tying a knot, the method comprising:
   passing a free suture limb of a length of suture through the tissue, the length of suture also having a fixed suture limb, secured to a rigid anchor body;
   drawing the free suture limb through a suture tunnel formed adjacent the fixed suture limb, the suture tunnel extending along an external surface of the rigid anchor body intermediate a proximal and distal end of the rigid anchor body, and thereby defining a closed suture loop around the tissue;
   inserting the anchor body into a bone hole, so as to concurrently compress a portion of the length of suture between an internal wall of the bone hole and an exterior feature of the anchor body thereby locking the closed suture loop so as to prevent tissue pull-out.

2. The method of claim 1 further comprising drawing the tissue towards the anchor body by pulling on the free suture limb.

3. The method of claim 2 wherein the tissue is drawn towards the anchor body by pulling on the free suture limb after the anchor body has been inserted into the bone hole.

4. The method of claim 1 wherein the fixed suture limb is secured to an exterior of the anchor body.

5. The method of claim 1 wherein the fixed suture limb and suture tunnel are disposed along the anchor body and at a location along the anchor body that is axially coincident with each other.

6. The method of claim 1 wherein inserting the anchor body into the bone hole further comprises locking the anchor body within the bone hole with at least one bone locking feature selected from the group consisting of a barb, ridge, thread, and rib.

7. The method of claim 1 wherein the suture fixed limb is secured to the anchor body via bonding, ultrasonic welding, ultrasonic staking, heat staking, ultrasonic molding, or injection molding the anchor body to the suture.

8. A method of anchoring a tissue to a bone of a human or an animal without tying a knot, the method comprising:
passing a free suture limb of a length of suture through the tissue, the length of suture also having a fixed suture limb, secured to an anchor body;
drawing the free suture limb through a suture tunnel formed in the vicinity of the fixed suture limb, the suture tunnel extending along an external surface of the anchor body intermediate a proximal and distal end of the anchor body, and thereby defining a suture loop around the tissue;
inserting the anchor body into a bone hole; and
locking the suture loop so as to prevent tissue pull-out.

9. The method of claim 8 further comprising compressing a portion of the length of suture between an internal wall of the bone hole and the exterior surface of the anchor body.

10. The method of claim 8 further comprising drawing the tissue towards the anchor body by pulling on the free suture limb.

11. The method of claim 9 wherein the tissue is drawn towards the anchor body by pulling on the free suture limb after the anchor body has been inserted into the bone hole.

12. The method of claim 8 wherein the fixed suture limb is secured to an exterior of the anchor body.

13. The method of claim 8 wherein fixed suture limb and suture tunnel are disposed along the anchor body and are axially coincident each other.

14. The method of claim 8 wherein inserting the anchor body into the bone hole further comprises locking the anchor body within the bone hole with at least one bone locking feature selected from the group consisting of a barb, ridge, thread, and rib.

15. A method of tissue repair, comprising:
installing an anchor body in bone, the anchor body having a suture extending along at least a portion of the anchor body and a snare device extending along a suture tunnel of the suture, the suture tunnel fixed to the anchor body intermediate a proximal and distal end of the anchor body;
forming, with the suture and the snare device, a knotless closed loop having an adjustable perimeter, the closed loop including the suture tunnel.

16. The method of claim 15, further comprising adjusting the length of the knotless closed loop to approximate tissue to bone.

17. The method of claim 15, further comprising:
installing the anchor body into a hole in the bone.

18. The method of claim 15, further comprising;
passing a free end of the suture through tissue to be fixated, and then through an eyelet of the snare device; and
pulling on the snare device to allow the suture free end to extend through the suture tunnel.

19. The method of claim 15 wherein the suture includes a suture fixed limb secured to an exterior of the anchor body intermediate the proximal and distal end of the anchor body.

20. The method of claim 19 wherein the suture fixed limb and suture tunnel are disposed along the anchor body and are axially adjacent each other.

* * * * *